(12) United States Patent
Mohiuddin et al.

(10) Patent No.: US 6,364,864 B1
(45) Date of Patent: Apr. 2, 2002

(54) PLASTIC CONTAINERS HAVING INNER POUCHES AND METHODS FOR MAKING SUCH CONTAINERS

(75) Inventors: Mahmood Mohiuddin, Hawthorn Woods, IL (US); George D. Cimino, Lafayette; Derek J. Hei, Concord, both of CA (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/325,436

(22) Filed: Jun. 3, 1999

(51) Int. Cl.[7] .......................... A61B 19/00; B65D 25/08
(52) U.S. Cl. ................... 604/410; 604/408; 604/416; 206/219
(58) Field of Search .................. 604/408, 410, 604/416, 82, 87; 206/219, 220, 221, 222

(56) References Cited

U.S. PATENT DOCUMENTS

| | | | |
|---|---|---|---|
| 2,766,907 A | * 10/1956 | Wallace, Jr. ............... 604/410 |
| 3,221,741 A | 12/1965 | LeVeen | |
| 3,692,493 A | 9/1972 | Terasaki | |
| 4,035,304 A | 7/1977 | Watanabe | |
| 4,066,556 A | 1/1978 | Vaillancourt | |
| 4,073,723 A | 2/1978 | Swank et al. | |
| 4,092,246 A | 5/1978 | Kummer | |
| 4,162,676 A | 7/1979 | Talcott | |
| 4,235,233 A | 11/1980 | Mouwen | |
| 4,396,383 A | 8/1983 | Hart | |
| 4,437,472 A | 3/1984 | Naftulin | |
| 4,458,733 A | 7/1984 | Lyons | |
| 4,467,588 A | * 8/1984 | Carveth ............... 604/410 |
| 4,484,920 A | 11/1984 | Kaufman et al. | |
| 4,507,114 A | 3/1985 | Bohman et al. | |
| 4,608,043 A | * 8/1986 | Larkin ............... 604/87 |
| 4,776,455 A | 10/1988 | Anderson et al. | |
| 4,834,743 A | 5/1989 | Valerio | |
| 4,880,425 A | 11/1989 | Kuhlemann et al. | |
| 4,900,321 A | 2/1990 | Kaufman et al. | |
| 4,976,707 A | 12/1990 | Bodicky et al. | |
| 4,997,083 A | 3/1991 | Loretti et al. | |
| 5,024,536 A | 6/1991 | Hill | |
| 5,049,146 A | 9/1991 | Bringham et al. | |
| 5,080,747 A | 1/1992 | Veix | |
| 5,100,401 A | 3/1992 | Patel | |
| 5,176,634 A | 1/1993 | Smith et al. | |
| 5,267,646 A | * 12/1993 | Inoue et al. ............... 206/204 |
| 5,354,262 A | 10/1994 | Boehringer et al. | |
| 5,373,966 A | 12/1994 | O'Reilly et al. | |
| 5,423,421 A | * 6/1995 | Inoue et al. ............... 206/219 |
| 5,462,526 A | 10/1995 | Barney et al. | |
| 5,507,525 A | 4/1996 | Leuenberger | |
| 5,514,106 A | 5/1996 | D'Silva | |
| 5,543,062 A | 8/1996 | Nishimura | |
| 5,560,403 A | 10/1996 | Balteau et al. | |
| 5,562,836 A | 10/1996 | Joie et al. | |
| 5,610,170 A | * 3/1997 | Inoue et al. ............... 514/340 |
| 5,695,489 A | 12/1997 | Japuntich | |
| 5,724,988 A | 3/1998 | Dennehey et al. | |
| 5,772,644 A | 6/1998 | Bark et al. | |
| 5,772,880 A | 6/1998 | Lynn et al. | |
| 5,785,700 A | 7/1998 | Olson | |
| 5,792,133 A | * 8/1998 | Rochat ............... 604/406 |
| 5,824,216 A | 10/1998 | Joie et al. | |
| 5,843,049 A | 12/1998 | Heilmann et al. | |
| 5,858,015 A | 1/1999 | Fini | |
| 5,910,138 A | 6/1999 | Sperko et al. | |
| 5,928,213 A | 7/1999 | Barney et al. | |

FOREIGN PATENT DOCUMENTS

| | | |
|---|---|---|
| EP | 0 526 678 A1 | 10/1993 |
| WO | WO 96/40857 | 12/1996 |

* cited by examiner

Primary Examiner—Angela D. Sykes
Assistant Examiner—Patricia Bianco
(74) Attorney, Agent, or Firm—Andrew G. Kolomayets; Michael C. Mayo

(57) ABSTRACT

Containers and methods for making containers are disclosed. The containers include a chamber and a pouch fixed within the chamber. During manufacture, the open edges of the pouch are sealed between the walls of the container by a seal defining, in part, the peripheral edge of the chamber.

7 Claims, 2 Drawing Sheets

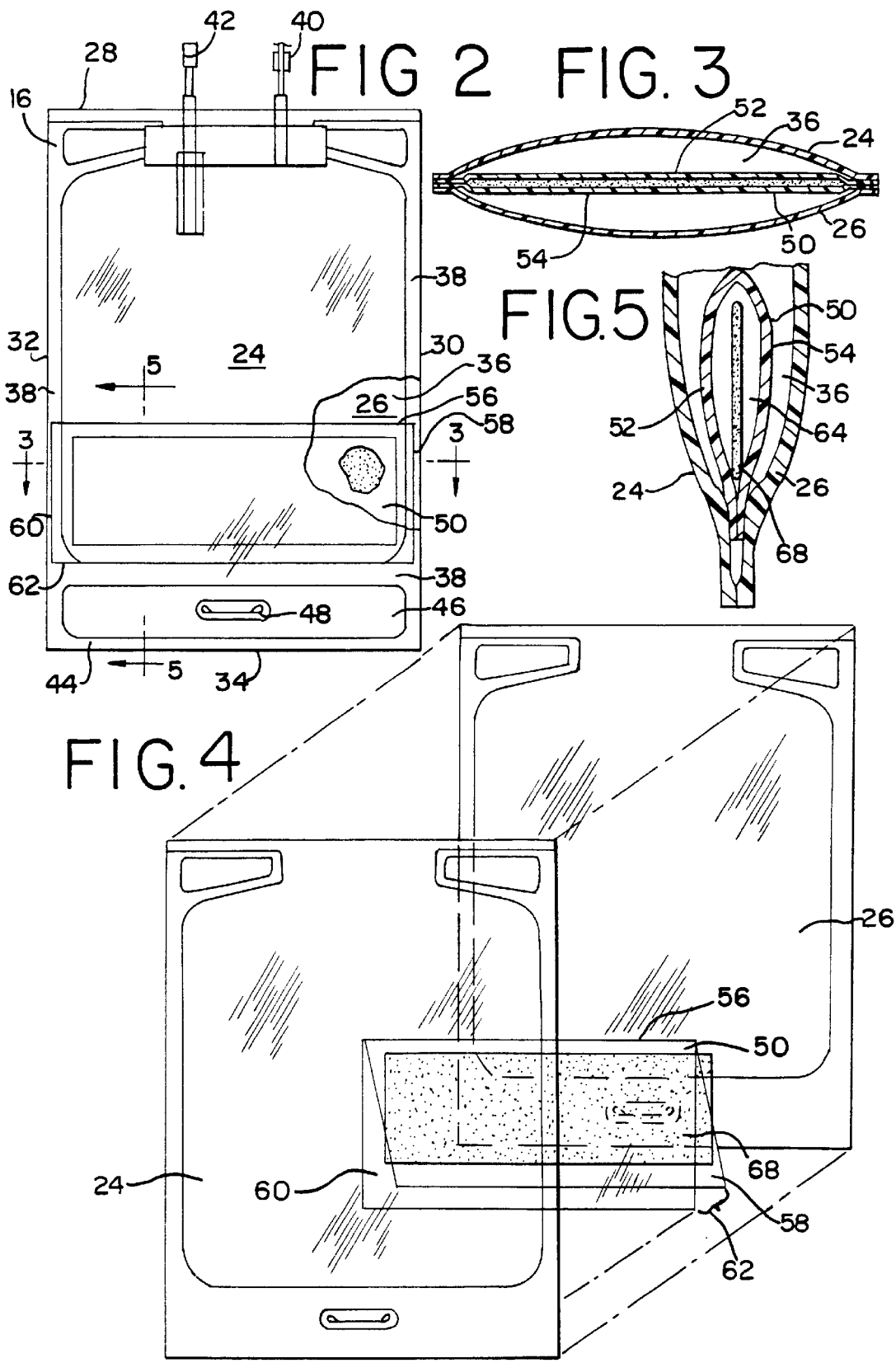

PLASTIC CONTAINERS HAVING INNER POUCHES AND METHODS FOR MAKING SUCH CONTAINERS

BACKGROUND OF THE INVENTION

The present invention relates generally to plastic containers having an inner pouch fixed within an outer chamber and, more particularly, to such containers and to methods for making such containers that are especially, although not exclusively, useful in liquid storage or processing applications such as the processing, storing and treating of biological fluids such as blood and blood components In the medical field, plastic containers having outer and inner pouches and/or compartments are known. For example, International Publication No. WO 96/40857 discloses containers useful for removing certain compounds in blood products that have been treated to inactivate pathogens in the blood products. The containers disclosed therein include an outer plastic container and an inner free floating pouch typically made of a liquid permeable mesh.

The mesh pouches may contain an adsorbent material capable of removing certain compounds used in the pathogen inactivation process. The outer chamber receives the blood product that has been subjected to the pathogen inactivation process. The liquid permeable mesh allows the blood product to contact the adsorbent, while retaining the adsorbent with the pouch.

The pouches are typically made of two sheets of mesh material sealed together along their peripheral edges or a single sheet of a folded mesh material sealed along a portion of its peripheral edge. The reliability of the seal along the peripheral edges of the pouch is important to ensure that adsorbent material does not enter the chamber where the blood product is retained.

U.S. Pat. No. 4,976,707 discloses a fluid storage apparatus which includes an inner flexible container enclosed within an outer flexible container. The interior container may hold a liquid, and the outer container may be filled with gas or air to exert pressure on the interior container and thereby expel the liquid from the interior container. In one embodiment, the peripheral edges of the interior container and exterior container are sealed together, forming an integral multicompartment container.

U.S. Pat. No. 4,235,233 discloses a blood bag having an upper fluid storage portion and a lower filter portion that includes a filter media. The storage portion is separated from the filter portion by a temporarily sealed outlet. The seal may be broken to allow blood to flow from the upper storage portion into the lower filter portion and, more specifically, through the filter media. As shown in FIGS. 5 and 6 of the '233 patent, at least the two side edges of the filter portion are sealed between the side edges of the blood bag, the bottom edge of the filter media is either the fold of the filter media or a seal, and the top edge contains an inlet tube for liquid flow through filter.

Although the above described containers may have worked satisfactorily for their intended purposes, further improvements in reliability and in the ease of manufacturing such containers are desirable.

SUMMARY OF THE INVENTION

The present invention, in one aspect, is embodied in a container having a first wall and a second wall joined to define an outer liquid receiving chamber having a peripheral edge. The peripheral edge is defined, at least in part, by a seal between the first and second walls. The container includes a pouch fixed within the liquid receiving chamber. The pouch includes first and second facing walls joined to define an inner chamber. In one aspect of the present invention, at least a portion of the first and second inner pouch walls are liquid permeable. The inner chamber is closed to the exterior except through the liquid permeable portion. The pouch walls are located between the first and second outer chamber walls and are sealed with the first and second walls along a portion of the seal.

In another aspect of the present invention, the inner pouch is made of a folded sheet of a polymeric material. The polymeric material may be made of a biocompatible material such as polyester. The container may be made of a thermoplastic material including, but not limited to, a blend of polymers and/or copolymers. In another aspect of the present invention, the melting point of the thermoplastic material is lower than the melting point temperature of the polymeric material of the inner pouch.

In one aspect of the present invention, the container includes first and second walls of a thermoplastic material joined to define a liquid receiving chamber having opposed side edges and opposed end edges defined by lines of seal between the first and second walls. The container includes a pouch fixed within the liquid receiving chamber. The pouch is made from a single sheet of a polymeric material folded along a fold line to form facing panels having opposed end edges and opposed side edges. One of the end edges is defined by the fold line and the other end edge and side edges are sealed, respectively by the line of seal defining one of the end edges and the side edges of the liquid receiving container to define a closed interior chamber within the pouch.

The present invention is also directed to a method for making a plastic container. The method includes providing two sheets of a thermoplastic material. The method further includes forming a pouch including two facing walls defining a pouch chamber, a closed edge and an oppositely disposed open edge. At least a portion of the pouch walls are liquid permeable. The pouch walls are located between the two thermoplastic sheets. A seal is formed between the sheets and the pouch walls are captured at the open pouch edge within the seal, whereby the pouch chamber is closed to the exterior except for the liquid permeable portion.

In another aspect of the present invention, the inner pouch is formed by folding a sheet of a porous polymeric material. The pouch includes a chamber defined by two facing walls and includes a closed edge and one or more open edges. The crease of the fold provides the closed edge while the one or more remaining edges of the pouch are open. The pouch is placed between the first and second sheets of thermoplastic material so that the one or more open edges of the pouch are substantially co-incident with the peripheral edges of the thermoplastic sheets that will define a liquid holding chamber. The thermoplastic sheets are sealed together substantially at the peripheral edges to provide an outer liquid holding chamber and to seal the remaining one or more open edges of the inner pouch.

BRIEF DESCRIPTION OF THE DRAWINGS

FIG. 2 is a perspective view of a container in accordance with the present invention with a portion broken away to show the inner pouch;

FIG. 3 is a cross-sectional view of the container of FIG. 2 taken along 3—3;

FIG. 4 is an exploded view of the container of the present invention; and

FIG. 5 is a cross-sectional view of a portion of container of FIG. 2 taken along 5—5.

DETAILED DESCRIPTION OF THE DRAWINGS

Figure 1:
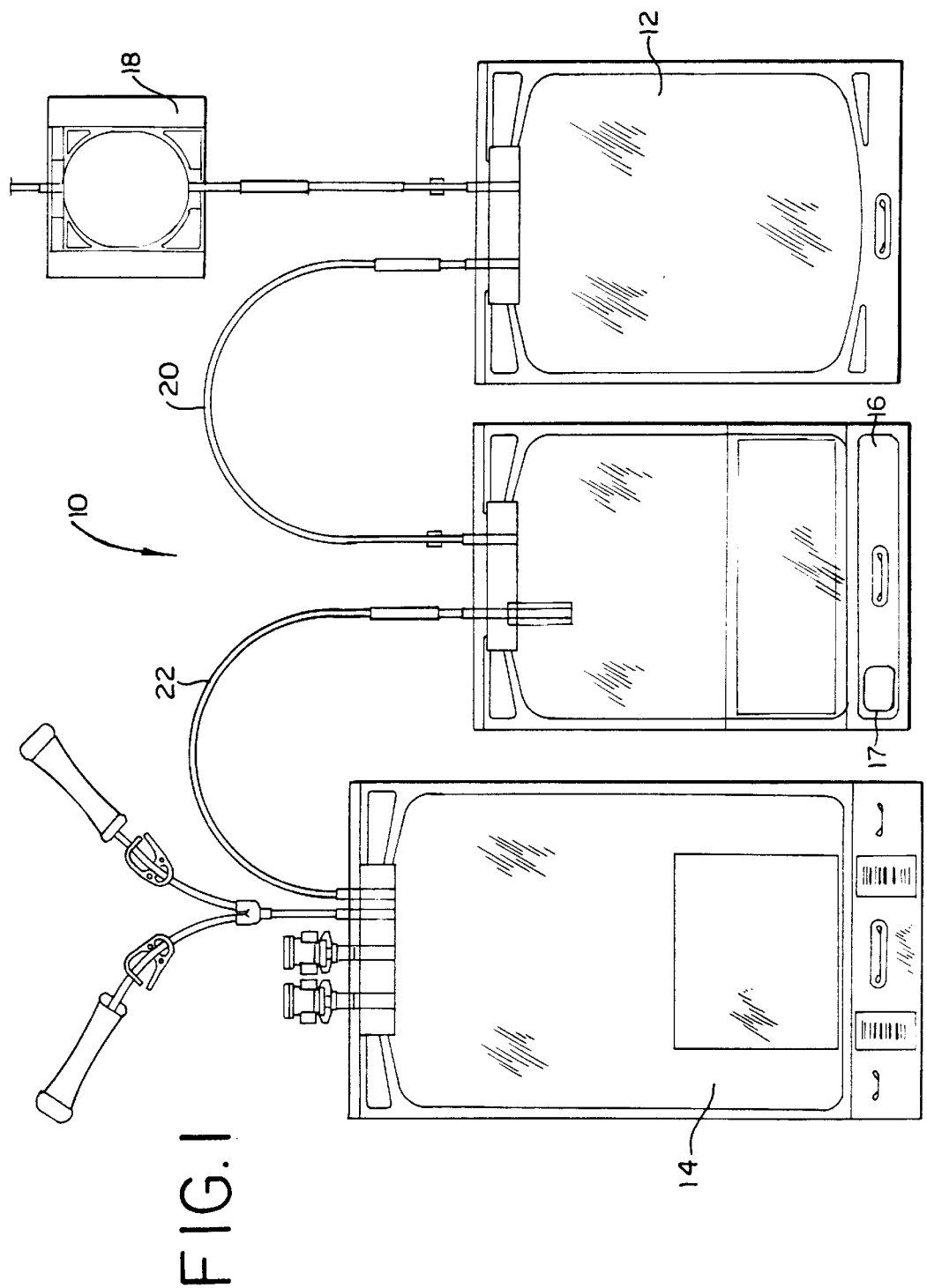
FIG. 1 is a perspective in view of the disposable tubing set including a container in accordance with the present invention.

For purposes of illustration, the present invention will be described, in large part, in connection with its preferred use as a container for holding a biological fluid and, more specifically, as a container for holding blood platelets that have been treated in a pathogen inactivation process. However, it should be recognized that the containers and methods for making containers in accordance with the present invention have applications beyond the field of blood treatment and, indeed, beyond the medical field. Containers of the present invention may have application in any field wherein it is desirable to provide a plastic container having an inner pouch. For example, containers of the present invention may be used in other applications where it would be desirable to contact the liquid in the container with the contents of an inner pouch. Thus, the following discussion should not be construed as limiting the present invention to the particular applications and uses described below.

Turning now to the drawings, FIG. 1 shows a disposable tubing and container set 10 useful, for example, in the method for inactivating pathogens that may be found in blood components such as blood platelets and/or blood plasma. Disposable tubing and container set 10 includes inactivation container 12, storage container 14 and a processing container 16 which may be a container embodying the present invention. Disposable tubing and container set 10 may further include a container 18 for holding compounds used in a pathogen inactivation process and tubing 20 and 22 connecting container 12 and 16 and 16 and 14 respectively. A more detailed discussion of the disposable tubing and container set is set forth in U.S. patent application Ser. No. 09/325,599, entitled "Processing Set and Methods for Processing and Treating a Biological Fluid", filed Jun. 3, 1999, in the names of Serge de Gheldere, Mahmood Mohiuddin, Peyton S. Metzel, George D. Cimino, Derek J. Hei and Michael S. Clark, and incorporated by reference herein in its entirety.

Although a detailed discussion of the pathogen inactivation process for which disposable tubing and container set 10 is used is beyond the scope of the present invention, a brief overview is provided. In general, either during or after collection of whole blood from a donor, a blood component such as platelets and/or plasma is separated from whole blood by centrifugation, membrane separation or other methods which are known to those of skill in the art. The separated blood component and pathogen inactivation compound from container 18 are introduced into inactivation container 12 in a predetermined ratio. In accordance with one method of treating blood platelets, the platelets are combined with a pathogen inactivation compound such as a photochemical agent. The combination of platelets and photochemical agent is exposed to a light of a wavelength and intensity sufficient to activate the agent which, in turn, results in the inactivation of pathogens present in the blood component. At least one such treatment method is described in International Publication No. WO 96/40857, which is incorporated by reference herein in its entirety.

After inactivation, the blood component is transferred through tubing 20 to processing container 16 where any remaining photochemical agent and/or other undesired byproducts of the pathogen inactivation process are removed. Typically, as described in International Publication No. WO 96/40857, the photochemical agent and any such byproducts are removed from the blood component by allowing the fluid in container 16 to contact an adsorbent substance which selectively removes the undesired compounds without removing or harming the desired components (e.g., platelets, plasma proteins). Container 16 may also include bar codes, time sensitive tabs or other indicia 17 to indicate the status of processing within container 16 as described in the above-identified application. After removal of the undesired compounds, the blood component may be transferred to storage container 14 via tubing 22 wherein, the component may be stored (with or without a storage medium) until administration of the component to a patient. In an alternative embodiment, processing container 16 may also serve as the storage container. Additional details of the pathogen inactivation process including removal of the photochemical agents and/or the byproducts are set forth in the above identified and incorporated by reference International Publication No. WO 96/40857.

Turning now to FIG. 2, the present invention, in one aspect, is embodied in container 16 which includes a first wall 24 and a second wall 26. Container 16 may be rectangular in shape and include top edge 28, side edges 30 and 32 and bottom edge 34. Of course, container 16 need not be rectangular and may have a square, oval or other desired shape. In any event, walls 24 and 26 are joined, such as by heat sealing, to define a chamber 36 for holding a liquid or fluid. As shown in FIG. 2, chamber 36 has a peripheral edge defined by the seal line 38 between the facing walls. In a preferred embodiment, seal line 38 may be substantially straight as shown in FIG. 2. Typically, container 16 may also include access ports 40 and 42 of standard construction through which liquid may be introduced and/or removed.

Container 16 may also include an additional seal 44, which as shown in FIG. 2, together with seal line 38 define a distal end portion or tail flap 46 of container 16. End portion 46 may include a slit 48 to allow container 16 to be suspended from a hook or the like. Of course, it should be understood that end portion 46 is optional and depending on the desired shape and size of chamber 36, seal line 38 may be spaced from the edges of container 16. Depending on the use, container 16 and more particularly liquid receiving chamber, may be of any desired size. For example, where container 16 is used for holding a biological fluid such as blood or a blood component, the size of liquid receiving chamber may be sufficient to hold between approximately 500–1500 ml of the biological fluid.

Container walls 24 and 26 may be made of any material that is suitable for the particular application for which container 16 is used, and which is a capable of being sealed by available sealing techniques. Preferably, container walls 24 and 26 may be made of a substantially transparent, thermoplastic material. Walls 24 and 26 may be plies or sheets obtained from an extruded film of thermoplastic material.

Where container 16 is used in medical applications, such as the blood treatment methods described above, container walls 24 and 26 are preferably made of a biocompatible, thermoplastic material. Moreover, where container 16 is used for the storage of blood components such as platelets, walls 24 and 26 should be made of a flexible, transparent, biocompatible, thermoplastic material having sufficient gas ($O_2$ and $CO_2$) permeability to allow the blood components to retain their viability during a typical storage period. The thickness of walls 24 and 26 may be whatever thickness is required or desired for the intended use of container 16.

Where container 16 is used for storing blood platelets, it is preferable that walls 24 and 26 have a thickness of between approximately 5 and 15 mils, and more preferably approximately 10±0.5 mils. Also, the materials used for walls 24 and 26 should be sterilizable by known sterilization techniques.

Preferred among the materials for walls 24 and 26 are blends of thermoplastic polymers and copolymers, including general purpose polymers, elastomers and the like. One such material includes a block copolymer which includes a central block of ethylene and butylene and terminal blocks of polystyrene. Block copolymers of the type described above are available from the Shell Chemical Co. and sold under the name KRATON. The block copolymer may be blended with other polymers or copolymers such as ultra low density polyethylene and ethylene vinyl acetate. A container made of the above described blend of block copolymer, ultra low density polyethylene and ethylene vinyl acetate is available from Baxter Healthcare Corporation of Deerfield, Ill. under the name PL-2410. Other thermoplastic materials may also be suitable for use in the present invention. For example, on such material (used in a container known as PL-732, also available from Baxter Healthcare Corporation) includes a block copolymer of the type described above, ethylene vinyl acetate and polypropylene.

Containers and the materials used to make such containers are typically sterilized by gamma or electron beam sterilization. Of course, any other polymer, copolymers or blends thereof which are biocompatible and have suitable properties for storage may also be used. Where container 16 is used in other applications, polymers such as polyvinyl chloride (typically with a plasticizer) may also be used.

As shown in FIGS. 2 and 3, in accordance with the present invention container 16 includes a pouch 50 located within liquid holding chamber 36. Pouch 50 may include facing walls 52 and 54 joined to define an inner chamber 64 (FIG. 5). Pouch 50 is preferably, but not necessarily, rectangular or square in shape and includes top edge 56, side edges 58 and 60 and bottom edge 62. Of course, it will be understood that pouch 50 may also have a different shape such as a half circle with a straight top edge and an arcuate bottom edge. In one embodiment, at least a portion of walls 52 and/or 54 may be liquid permeable. Where it is intended that liquid in chamber 36 achieve maximum and substantially uniform contact with the contents of pouch 50, it may be desirable that walls 52 and 54 be liquid permeable in their entirety. As set forth above, pouch 50 and, more specifically, walls 52 and 54 may be made in whole or in part of a liquid permeable material. Where container 16 is used in medical applications, walls 52 and 54 are made of a biocompatible material. One such material is polyester and more specifically a polyester mesh made from woven polyester fibers that allows liquid from chamber 36 to permeate walls 52 and 54. One such polyester mesh material is available from Tetko of Briarcliff Manor, N.Y. and is sold under the name MEDIFAB® 07-30-21. The polymeric material should have a sufficient pore size to allow for flow of liquid through the pores of the material. In one embodiment, the pore size of the mesh material may be less than 90 microns and, preferably, between approximately 10–80 microns and more preferably less than approximately 30 microns such as approximately 10 microns. A pore size of less than 90 microns and, preferably between approximately 10–80 microns or more preferably less than approximately 30 microns such as approximately 10 microns, will ensure that any solid material such as the adsorbent beads of the type described below, (which typically have a diameter of anywhere between 90–1400 microns) will not penetrate walls 52 and 54 of pouch 50 and enter chamber 36. Suitable polyester mesh materials are described in WO 96/40857, which has previously been incorporated by reference. Other materials that may be used are fibrous polyamides such as nylon.

As shown in FIG. 5, inner chamber 64 of pouch 50 may contain a substance or material intended for contact with the liquid in outer chamber 36. For example as described above, in an embodiment where container 16 is used to hold and store pathogen inactivated blood platelets and remove undesirable compounds or agents from a pathogen inactivation process, chamber 64 may include a treating material such as an adsorbent material. The adsorbent material may be in solid form, such as a suitable resin. The resin may be in a particulate form such as a powder, loose beads or, as shown in FIGS. 3–5, in the form of a solid support 68 with adsorbent beads affixed thereto. Adsorbent beads suitable for use in this embodiment include polystyrene/polydivinyl benzene beads available from Dow Chemical Co. and sold under the name DOWEX OPTIPORE® L-493. The amount of adsorbent will depend on the process. In one embodiment, the amount of adsorbent included is preferably approximately 2.5±0.1 grams. Additional examples of adsorbent materials and the details thereof are provided in International Publication No. WO 96/40857. Of course, the present invention is not limited to applications where the material in the pouch is an adsorbant material, whatever the form. The present invention comprehends situations where other materials may be used for entirely different purposes and is not limited to materials and purposes described herein as the preferred embodiment.

Turning now to the method of making container 16, two sheets or plies of thermoplastic material that will provide walls 24 and 26 are brought together in facing arrangement as substantially shown in FIG. 4. (Although the walls 24 and 26 shown in FIG. 4 show a seal line along the peripheries of walls 24 and 26, it should be understood that at the outset of the manufacturing process, walls 24 and 26 do not have seal lines and are typically flat sheets of the thermoplastic material.) Alternatively, walls 24 and 26 may be provided by folding a single sheet of thermoplastic material along a fold line to form two facing sheets or panels, with the fold line forming one edge of such a container. Next, pouch 50 is interposed between walls 24 and 26.

In a preferred embodiment, pouch 50 is formed by folding a square or rectangular sheet of a porous, liquid permeable material along a fold line to form facing sheets or panels and interposing the folded sheet between walls 24 and 26 shown in FIG. 4. In the preferred embodiment, the folded sheet is interposed between walls 24 and 26 with top edge 56 closed, by for example, the crease of the fold and the remaining edges 58, 60 and 62 open. These remaining open edges 58, 60 and 62 are aligned so as to be substantially co-incident with what will become the peripheral edge of chamber 36 as defined by seal line 38, so that the step of sealing side edges 30 and 32 of walls 24 and 26 also captures and seals open edges 60 and 58 of pouch 50, thereby fixing pouch 50 within chamber 36.

If material, such as adsorbent material, is to be introduced into chamber 64 of pouch 50, the material may then be introduced through the end of the container. The remaining open edge of chamber 36 and open edge 62 of pouch 50 may then be sealed along seal line 38. Alternatively, the treating material may be introduced into interior chamber 64 before any of the edges are sealed. Methods for filling pouch 50 are described in WO 96/40857.

In another alternative embodiment, pouch 50 may be formed by joining two sheets of the pouch material and sealing the sheets together along some or all of the edges 56, 58, 60 and 62. Of course, it will be understood that where pouch 50 is introduced into chamber 36 of container 16 as a pre-sealed pouch, inner chamber 64 must be filled with the desired material (if any) prior to sealing. Tubing ports 40 and 42 are formed in the upper edge of the container in standard fashion and formed before or after introduction of pouch 50.

Any suitable method of sealing walls 24 and 26 may be used, such as heat or solvent bonding. In one embodiment, it is preferred that walls 24 and 26 be heat sealed, preferably by impulse heat sealing, which is a sealing method well known to those of skill in the art. The temperature of the heat sealing method should be sufficient to melt the thermoplastic material of walls 24 and 26.

Where pouch 50 is a porous mesh material, it is desirable that the temperature of heat sealing not be substantially equal to or greater than the melting temperature of the mesh material. As presently understood, it is believed that the melted thermoplastic material of walls 24 and 26 flows through the open structure of the mesh material and forms a integral bond which "captures" the mesh material and forms a firm and integral bond with the pouch while simultaneously sealing the pouch walls together. Thus, where the pouch 50 is made of a polyester mesh material having a melting point of between 450–500° F., the temperature of heat sealing will be below this range. For example, in one embodiment where container 16 is formed by impulse heat sealing, the upper jaw or platen of the heat sealing apparatus has a temperature of approximately 420° F. and the lower jaw or platen of the heat sealing apparatus has a temperature of approximately 110° F. Of course, other thermoplastic materials and polymers for inner pouch 50 may require different temperatures.

The present invention has been described in accordance with the preferred embodiments. However, it will be understood that variations to the embodiment shown herein may be made without departing from the present invention which is specifically set forth in the appended claims.

That which is claimed:

1. A container comprising:

first and second walls of a thermoplastic material joined to define a liquid receiving chamber having a peripheral edge, said peripheral edge defined at least in part by a seal between said first and second walls; and a pouch fixed within said liquid receiving chamber, said pouch comprising first and second facing walls made of a fibrous polymeric material selected from the group consisting of polyester and polyamide and joined to define an inner chamber, said first and second pouch walls being liquid permeable, said inner chamber being closed to the exterior except through said liquid permeable walls, said pouch walls being located between said first and second outer chamber walls and sealed therewith along a portion of said seal.

2. The container according to claim 1 wherein said pouch comprises a folded sheet of said polymeric material.

3. The container according to claim 1 wherein said first and second pouch walls comprise a polyester mesh.

4. The container according to claim 1 wherein the polymeric material comprising said first and second walls of said liquid receiving chamber has a melting point lower than the melting point of the polymeric material of said pouch walls.

5. The container according to claim 1 wherein said first and second walls of said liquid receiving chamber are made of a biologically compatible material.

6. The container according to claim 5 wherein said polymeric material comprising said first and second walls has a melting point less than 450° F.

7. A container comprising:

first and second walls of a thermoplastic material joined to define a liquid receiving chamber having opposed side edges and opposed end edges defined by a line of seal between said first and second walls; and a pouch fixed within said liquid receiving chamber, said pouch comprising a single sheet of a fibrous polymeric material selected from the group consisting of polyester and polyamide and folded along a fold line to form facing panels having opposed end edges and opposed side edges, one of said end edges being defined by said fold line, the other of said end edges and said side edges of said panels being sealed, respectively, by said line of seal defining one of said end edges and said side edges of said liquid receiving chamber to define an interior chamber within said pouch.

* * * * *